United States Patent
Kagerer et al.

(10) Patent No.: US 7,723,544 B2
(45) Date of Patent: May 25, 2010

(54) PROCESS FOR RECOVERY OF IOPROMIDE, SUITABLE FOR PHARMACEUTICAL PURPOSES, FROM MOTHER LIQUORS

(75) Inventors: Hartmut Kagerer, Selm (DE); Meike Dembeck, Datteln (DE); Hartmut Seba, Unna (DE); Ingo Ortmann, Werne (DE)

(73) Assignee: Bayer Schering Pharma AG, Berlin (DE)

( * ) Notice: Subject to any disclaimer, the term of this patent is extended or adjusted under 35 U.S.C. 154(b) by 30 days.

(21) Appl. No.: 11/633,087

(22) Filed: Dec. 4, 2006

(65) Prior Publication Data

US 2007/0265470 A1 Nov. 15, 2007

Related U.S. Application Data

(60) Provisional application No. 60/748,175, filed on Dec. 8, 2005.

(51) Int. Cl.
*C07C 233/77* (2006.01)
*C07C 233/87* (2006.01)

(52) U.S. Cl. .................................................. 564/153
(58) Field of Classification Search ................. None
See application file for complete search history.

(56) References Cited

U.S. PATENT DOCUMENTS 4,364,921 A 12/1982 Speck et al.

FOREIGN PATENT DOCUMENTS

EP 0015867 A1 9/1980
WO WO99/18054 * 4/1999

OTHER PUBLICATIONS

Krause et al. Topics in Current Chemistry 2002, v222, p. 107-150.*

* cited by examiner

*Primary Examiner*—Daniel M Sullivan
*Assistant Examiner*—Yevegeny Valenrod
(74) *Attorney, Agent, or Firm*—Millen, White, Zelano, Branigan, P.C.

(57) ABSTRACT

This invention describes a process for recovery of iopromide, suitable for pharmaceutical purposes, by heat treatment of the mother liquors or the secondary crystallizate in a reactor and subsequent crystallization.

8 Claims, 1 Drawing Sheet

Experimental Set-Up for Heat Isomerization of the Iopromide Secondary Crystallizate

PROCESS FOR RECOVERY OF IOPROMIDE, SUITABLE FOR PHARMACEUTICAL PURPOSES, FROM MOTHER LIQUORS

This application claims the benefit of the filing date of U.S. Provisional Application Ser. No. 60/748,175, filed Dec. 8, 2005.

The invention relates to a process for recovery of iopromide, suitable for pharmaceutical purposes, by heat treatment of mother liquors or dissolved secondary crystallizate in a reactor and subsequent crystallization.

Iopromide, 5-methoxyacetylamino-2,4,6-triiodo-isophthalic acid-[(2,3-dihydroxy-N-methyl-propyl)-(2,3-dihydroxypropyl)]-diamide, (DE 196 41 178 C and EP 0 015 867 B), is an iodine-containing x-ray contrast medium with the following chemical structure:

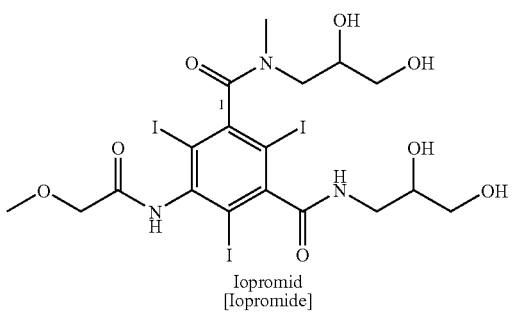

Iopromid
[Iopromide]

The bulky iodine atoms prevent, to a great extent, the free rotation of the bond, identified by 1 in the structural formula, between the aromatic ring and the amide group with the dihydroxypropyl-methylamino group by the presence of the N-methyl group, so that two atropisomers that are thermally quite stable occur. Such atropisomers are described in, i.a., "Recent Advances in Atropisomerism" by M. Oki in the journal "Topics in Stereochemistry," 1983, Volume 14, pages 1-81, and Tetrahedron Letters No. 38, pages 4593-4598, 1966. In the case of one of the atropisomers, the substituted nitrogen atom lies above the ring plane; with other isomers, it lies below the ring plane. The two atropisomeric compounds (isomer 1 and isomer 2) are different in their physical properties, especially in their solubilities in water and organic solvents. Only iopromide of a certain composition relative to these atropisomers is allowed as an x-ray contrast medium (40-51% isomer 1 and 49-60% isomer 2).

Iopromide for pharmaceutical purposes is obtained by crystallization from ethanol. In this connection, a mixture that consists of about 48% isomer 1 and about 52% isomer 2 accumulates regularly. The mother liquor contains the isomer 1 at about 60% and the isomer 2 at only up to about 40%. For this reason, only a secondary crystallizate with a false composition relative to the atropisomers can be recovered from the mother liquor (contains too much isomer 1).

In the production of iopromide, a final crystallization that consists of alcohol is performed herein. In this connection, a proportion of about 10% of iopromide remains in dissolved form in the mother liquor, which becomes apparent as a loss of yield.

Earlier tests—to crystallize out additional iopromide from the accumulating mother liquors by secondary crystallization and thus to increase the yield—failed, since the iopromide K2 recovered from the mother liquors is not in accordance with specifications with respect to the atropisomeric ratio. This behavior can be attributed to the fact that certain atropisomers preferably accumulate in the mother liquor.

OBJECT OF THE INVENTION

The production processes for iopromide that are known from the prior art herein exhibit the drawback that a higher loss in yield must be tolerated and no technical process exists that allows iopromide, which is in accordance with specifications with respect to the atropisomeric ratio and thus can be used for pharmaceutical purposes, to be recovered from the mother liquors.

RESOLUTION OF THE INVENTION

The above-described drawbacks could be resolved, surprisingly enough, in that first a K2 is recovered from the iopromide, pure mother liquor, by a suitable secondary crystallization, which then is isomerized in a continuous tubular-flow reactor in accordance with specifications by a suitable heat treatment, without significant decomposition of the substance occurring. The invention thus contains a process for recovery of iopromide and iopromide mother liquors, suitable for pharmaceutical purposes, or solutions of the secondary and subsequent crystallizates by heat treatment of the solution, preferably in a tubular-flow reactor at 100-300° C., advantageously at 200-220° C., and then quick cooling to room temperature and crystallization. The heat treatment in a flow reactor is advantageously carried out in aqueous solution at hydrodynamic dwell times of 1 to 60 minutes. The special embodiments are cited in the claims. The total yield of iopromide can be increased quite significantly by this process according to the invention, such that the economic efficiency increases. In addition, less halogen-containing waste accumulates.

DESCRIPTION OF THE PROCESS IN DETAIL

First, a secondary crystallizate is recovered from the iopromide, pure mother liquors, by the ethanolic mother liquors being concentrated by evaporation by the factor 2-16 and being dissolved in an alcohol at elevated temperature. Examples of suitable alcohols are alkanols such as methanol, ethanol, 1-propanol, 2-propanol, 1-butanol, and 2-butanol. Ethanol, 1-propanol and 2-propanol are preferably used, especially preferably 1-propanol, since the crystallization from this solvent takes place especially quickly and completely and thus is economical. To achieve the crystallization, it can be completely inoculated with iopromide. The K2 crystallizate is then isolated, washed and dried according to known methods.

Example 1

Production of the K2 Crystallizate 12,000 g of iopromide, pure mother liquor (solid content about 6.2%), is concentrated by evaporation in a vacuum to form viscous oil of 892 g. 877 g of this residue is mixed in a suitable reaction vessel at a bath temperature of 65° C. with 439 ml of 1-propanol while being stirred. After inoculation with 0.73 g of iopromide, it is fully stirred for another 48 hours at a bath temperature of 65° C. The crystal suspension is then cooled to 20° C., stirred for 1 hour at this temperature and suctioned off via a suction filter. After washing with 4 portions of 110 ml of ethanol, the secondary crystallizate is dried at 40° C. in a vacuum-drying oven.

Yield: 363.8 g (about 52% of the experiment)

The secondary crystallizate that is obtained from the mother liquor has the following atropisomeric ratio:

| HPLC | Specification | Result |
| --- | --- | --- |
| Isomer 1 | 40.0-51.0% | 62.2% |
| Isomer 2 | 49.0-60.0% | 37.8% |

The recovered secondary crystallizate is then brought into solution, i.e., dissolved in water and heat-isomerized in a pressure-resistant, suitably designed, continuously-operating tube reactor. In this connection, hydrodynamic dwell times of 1 to 60 minutes, preferably 1-30 minutes, especially preferably 1 to 10 minutes, are set at temperatures of between 100 to 300° C., preferably 150° C. to 250° C., preferably 180° C. to 230° C., especially preferably 200° C. to 220° C. In a downstream heat exchanger, the heat-treated iopromide K2 solution is then quickly cooled to room temperature.

Example 2

Heat-Isomerization of the Iopromide Secondary Crystallizate 280 g of iopromide-K2 from Example 1 is dissolved in 520 g of water. The solution is then pumped at a volumetric flow rate of 3 ml/minute through a flow pipe that is provided with a pressurization valve of 20 bar at 208-209° C. The flow pipe that is used has an inside diameter of 1.7526 mm and a heated length of 5.5 m (see FIG. 1).

A solution of the isomerized iopromide secondary crystallizate is then purified via ion-exchange columns and crystallized from ethanol.

The yield of the iopromide that is crystallized from ethanol is approximately 80% of the experiment relative to the secondary crystallizate that is used in the isomerization.

The crystallizate shows a content after HPLC (standard method) of greater than 97.5% relative to the external standard and has the following atropisomeric ratio:

| HPLC | Specification | Result |
| --- | --- | --- |
| Isomer 1 | 40.0-51.0% | 49.4% |
| Isomer 2 | 49.0-60.0% | 50.6% |

Figure 1:
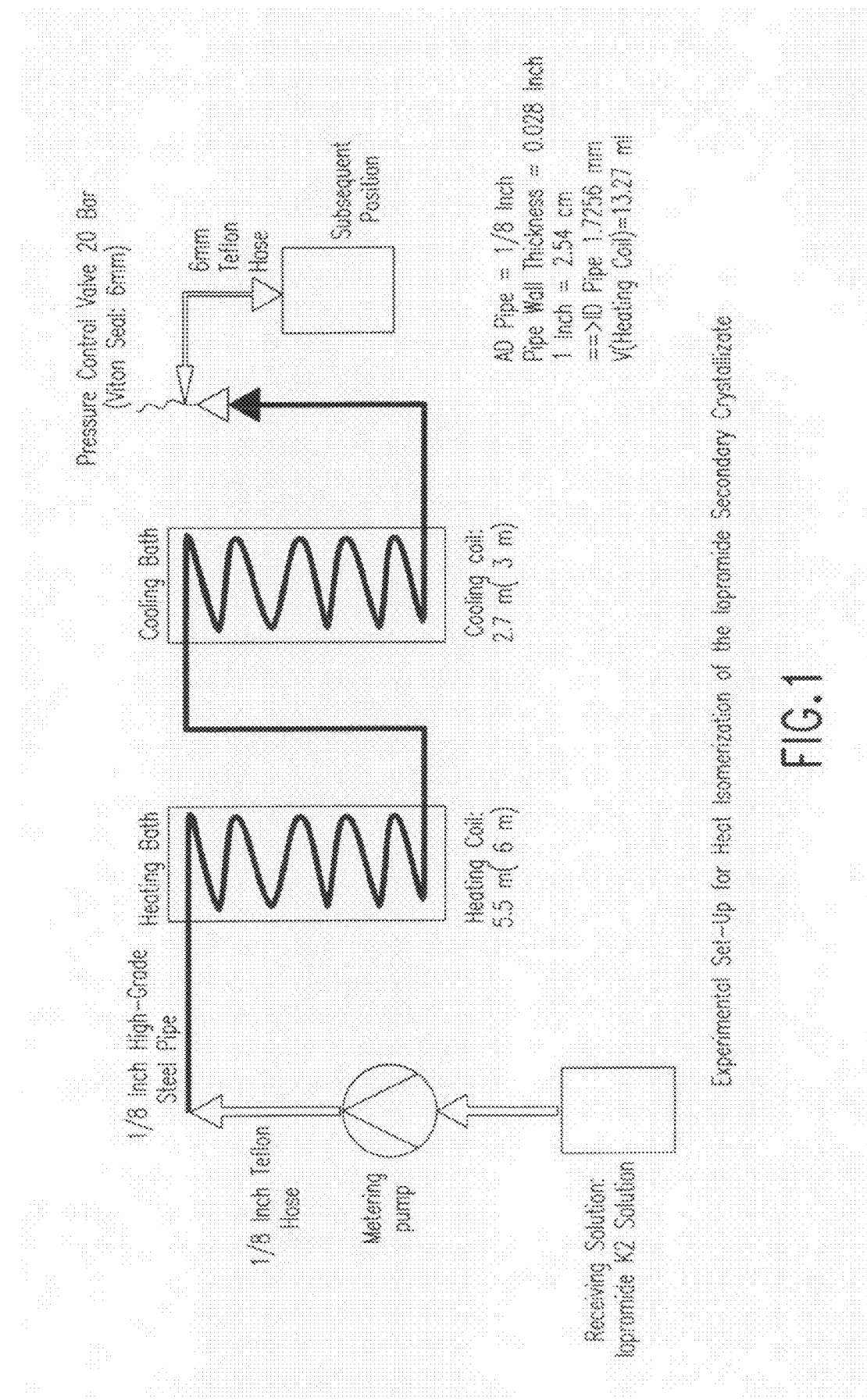
FIG. 1: Experimental Set-up for heat isomerization of the iopromide secondary crystallizate.

The invention claimed is:

1. A process for recovery of iopromide, comprising recovering iopromide suitable for pharmaceutical purposes, by crystallization of dissolved secondary or subsequent crystallizate from iopromide mother liquor, after heat treatment of said dissolved secondary or subsequent crystallizate in a tubular flow reactor wherein the iopromide suitable for pharmaceutical purposes contains atropisomeric forms in an amount of 40-51% isomer 1 and 49-60% isomer 2.

2. A process according to claim 1, in which iopromide that is contained in the mother liquor or the secondary or subsequent crystallizate has an isomeric ratio that is unsuitable for pharmaceutical purposes.

3. A process according to claim 1, in which the heat treatment in a tubular-flow reactor is carried out at 100-300° C.

4. A process according to claims 1, in which the crystallization is carried out from an alcohol.

5. A process according to claim 1, whereby the iopromide suitable for pharmaceutical purposes is obtained by temperature treatment of atropisomers that are dissolved in a solvent.

6. A process according to claim 5, whereby hydrodynamic dwell time of the atropisomers that are dissolved in a solvent in the tubular-flow reactor is 1 to 60 minutes.

7. A process according to claim 6, in which water is used as a solvent.

8. A process for recovery of iopromide, comprising crystallizing iopromide from mother liquor, dissolving said iopromide in a solvent, heat treating said dissolved iopromide in a tubular flow reactor, and crystallizing iopromide suitable for pharmaceutical purposes wherein the iopromide suitable for pharmaceutical purposes contains atropisomeric forms in an amount of 40-51% isomer 1 and 49-60% isomer 2.

* * * * *